United States Patent
Kano et al.

(10) Patent No.: US 9,576,358 B2
(45) Date of Patent: Feb. 21, 2017

(54) INDIVIDUAL-CHARACTERISTIC PREDICTION SYSTEM, INDIVIDUAL-CHARACTERISTIC PREDICTION METHOD, AND RECORDING MEDIUM

(71) Applicant: ARAYA BRAIN IMAGING INC., Tokyo (JP)

(72) Inventors: Yoshinobu Kano, Hamamatsu (JP); Ryota Kanai, Tokyo (JP)

(73) Assignee: ARAYA BRAIN IMAGING INC., Tokyo (JP)

( * ) Notice: Subject to any disclaimer, the term of this patent is extended or adjusted under 35 U.S.C. 154(b) by 0 days.

(21) Appl. No.: 14/900,685

(22) PCT Filed: Oct. 29, 2014

(86) PCT No.: PCT/JP2014/078818
§ 371 (c)(1),
(2) Date: Dec. 22, 2015

(87) PCT Pub. No.: WO2015/064665
PCT Pub. Date: May 7, 2015

(65) Prior Publication Data
US 2016/0155226 A1 Jun. 2, 2016

(30) Foreign Application Priority Data
Oct. 31, 2013 (JP) .................. 2013-226308

(51) Int. Cl.
*G06K 9/00* (2006.01)
*G06T 7/00* (2006.01)
(Continued)

(52) U.S. Cl.
CPC ........... *G06T 7/0012* (2013.01); *A61B 5/0042* (2013.01); *A61B 5/055* (2013.01); *A61B 5/4064* (2013.01);
(Continued)

(58) Field of Classification Search
CPC ............ G06T 2207/30016; G06T 2207/10088; G06T 7/0012; G06K 9/6289; G06K 9/00496; G06K 9/00536
See application file for complete search history.

(56) References Cited

U.S. PATENT DOCUMENTS

2009/0252391 A1   10/2009  Matsuda et al.
2011/0004092 A1    1/2011  Kato
(Continued)

FOREIGN PATENT DOCUMENTS

JP   2005-230456 A    9/2005
JP   2011-206452 A   10/2011
(Continued)

OTHER PUBLICATIONS

Dec. 16, 2014 International Search Report issued in International Patent Application No. PCT/JP2014/078818.

*Primary Examiner* — Jonathan S Lee
(74) *Attorney, Agent, or Firm* — Oliff PLC

(57) ABSTRACT

An individual-characteristic prediction system obtains three-dimensional information from brain images of a subject. Further, the individual-characteristic prediction system detects characteristic values of each part of the cerebrum of the subject, and compares the detected characteristic values with stored information prepared in advance to thereby search out stored information having characteristic values similar to the detected characteristic values. Further, the individual-characteristic prediction system predicts abilities or qualities of the subject based on information about (Continued)

abilities or qualities of a brain having the searched out characteristic values.

5 Claims, 11 Drawing Sheets

(51) Int. Cl.
 *A61B 5/055* (2006.01)
 *A61B 5/00* (2006.01)
 *G06F 19/00* (2011.01)
 *G01R 33/56* (2006.01)

(52) U.S. Cl.
 CPC .......... *A61B 5/7246* (2013.01); *A61B 5/7275* (2013.01); *A61B 5/742* (2013.01); *G06F 19/3437* (2013.01); *G06F 19/3443* (2013.01); *A61B 2560/0475* (2013.01); *A61B 2576/026* (2013.01); *G01R 33/5608* (2013.01); *G06T 2207/10088* (2013.01); *G06T 2207/30016* (2013.01)

(56) References Cited

U.S. PATENT DOCUMENTS

| 2012/0197105 | A1  | 8/2012  | Mezer et al. |                      |
|--------------|-----|---------|--------------|----------------------|
| 2013/0116540 | A1* | 5/2013  | Li           | A61B 5/055 600/410   |
| 2013/0259346 | A1* | 10/2013 | El-Baz       | G06T 7/0012 382/131  |
| 2015/0012466 | A1* | 1/2015  | Sapiro       | G06F 17/30244 706/12 |
| 2015/0088024 | A1* | 3/2015  | Sackellares  | A61B 5/0476 600/544  |
| 2016/0019693 | A1* | 1/2016  | Silbersweig  | G06T 7/0012 382/128  |
| 2016/0038049 | A1* | 2/2016  | Geva         | A61B 5/048 600/544   |
| 2016/0300352 | A1* | 10/2016 | Raj          | G06T 7/0016          |

FOREIGN PATENT DOCUMENTS

| WO | 2007/023522 A1 | 3/2007 |
| WO | 2009/005013 A1 | 1/2009 |

* cited by examiner

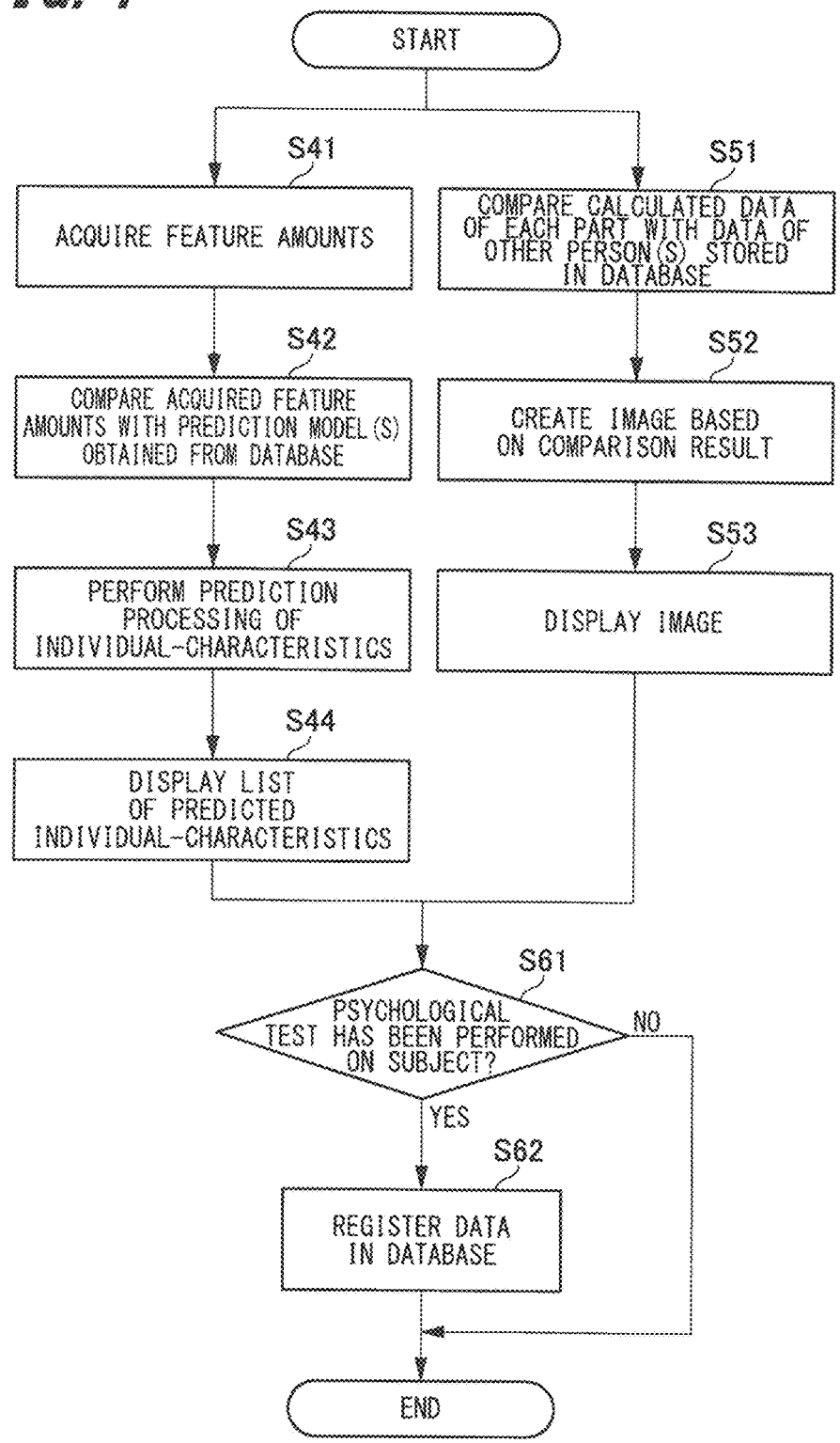

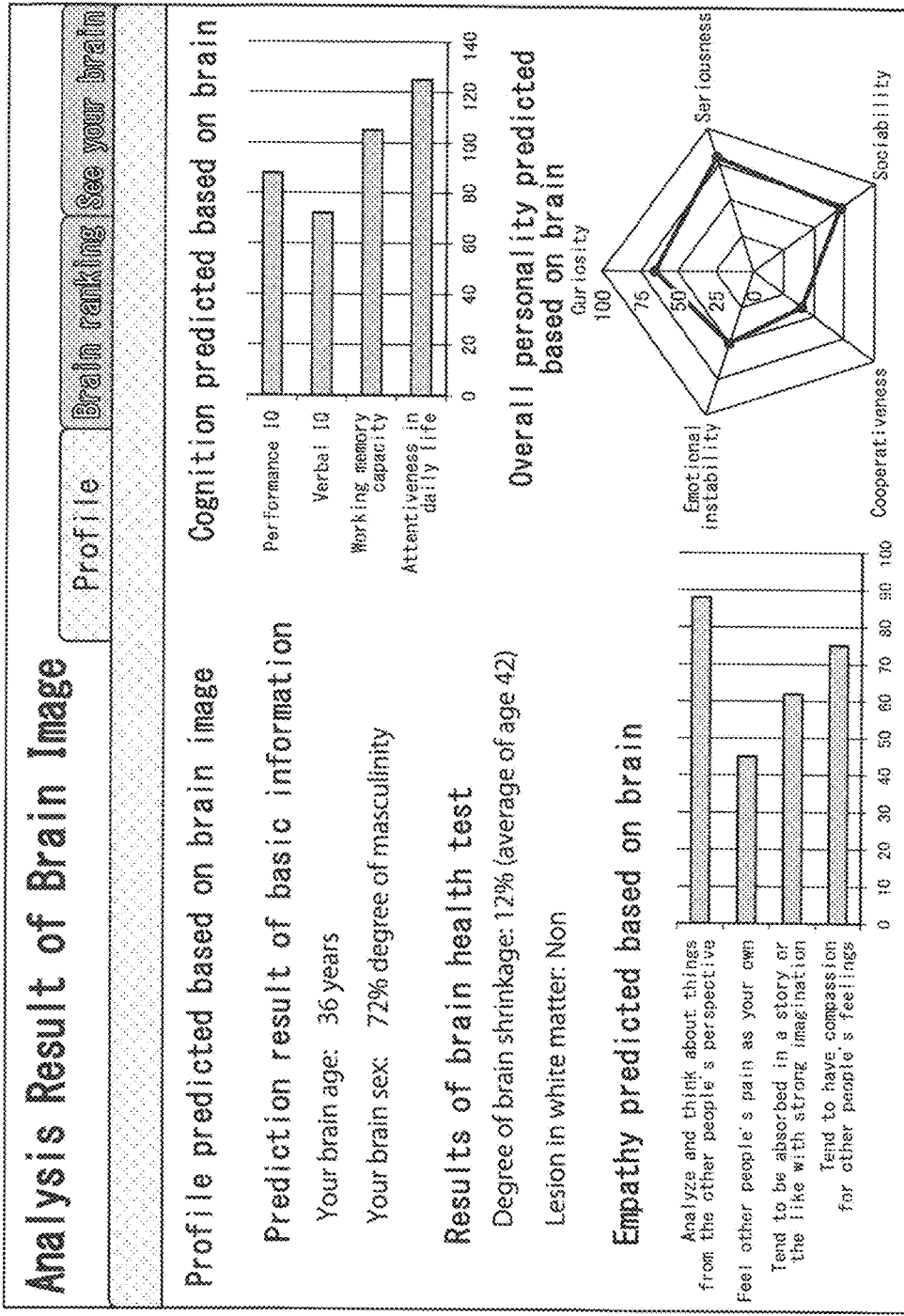

FIG. 6

Analysis Result of Brain Image

| Profile | Brain ranking | See your brain |

Top 3 of your brain volume

Rank 1st: Hippocampus (left) : Rank 3rd among 100 persons. Hippocampus plays important roles in long-term memory and spatial cognition.

Rank 2nd: Superior parietal lobule (right) : Rank 15th among 100 persons. Superior parietal lobule is involved with long-lasting attention and spatial orientation.

Rank 3rd: Peripheral area of calcarine sulcus (left & right) : Rank 18th among 100 persons. Peripheral area of calcarine sulcus is where the primary visual cortex (a part of the cerebral cortex which first receives the signal from the eyes) is located.

See more.

Bottom 3 of your brain volume

Rank 1st: Precuneus (left) : Rank 82nd among 100 persons. Precuneus plays active roles when imagining things, and is involved with empathy to have compassion for other people's feelings. As a matter of fact, the smaller the precuneus is, the higher the function it has.

Rank 2nd: Superior temporal sulcus (left) : Rank 74th among 100 persons. Superior temporal sulcus is involved in the perception of where others are gazing and where others' emotions are being directed.

Rank 3rd: Orbitofrontal cortex : Rank 64th among 100 persons. Orbitofrontal cortex is involved in sophisticated decision making, introspection of one's own and the like, and is particularly highly developed in human beings.

See more.

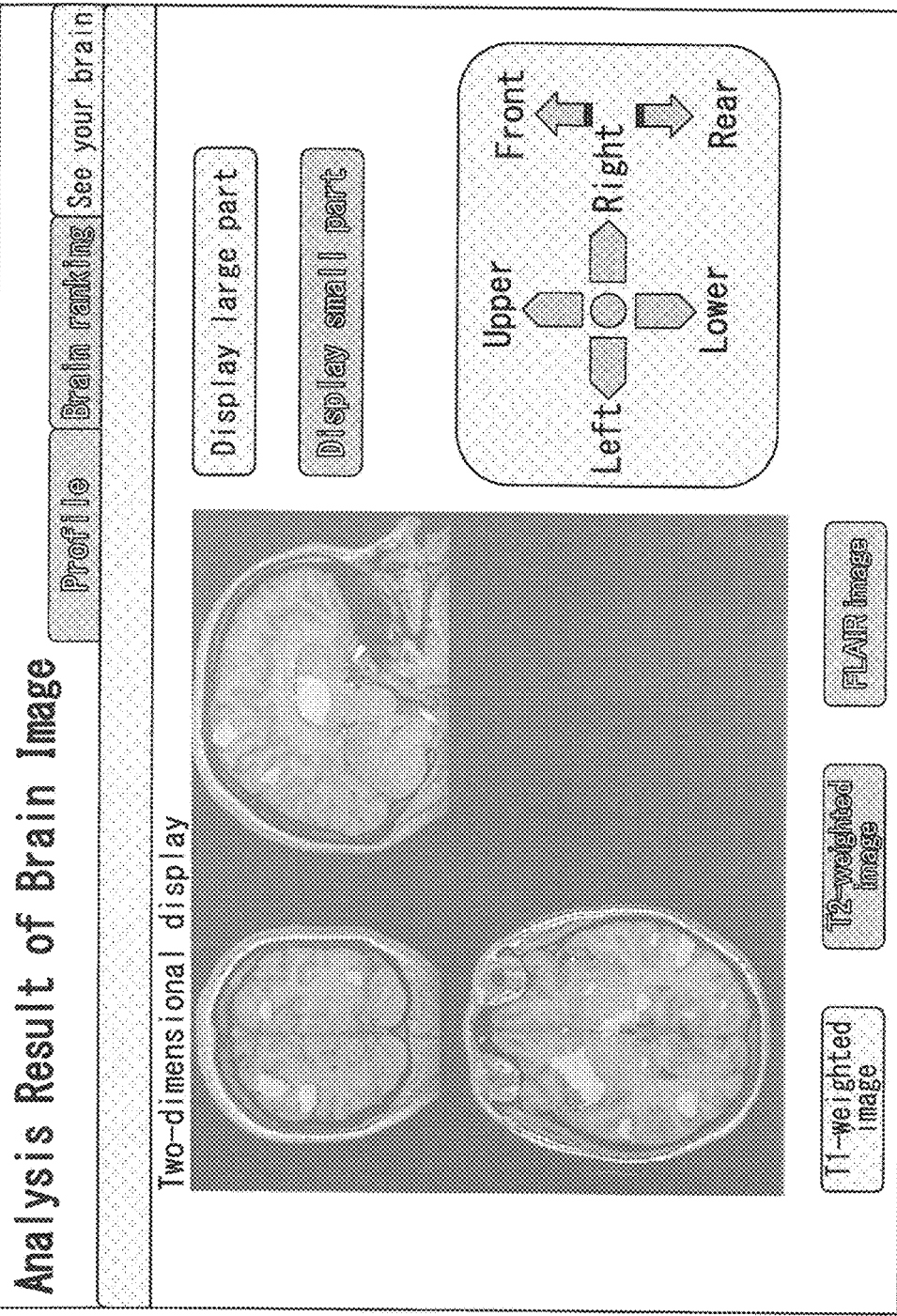

PREDICTION OF AGE BASED ON VOLUME
INFORMATION OF EACH PART OF ENTIRE BRAIN

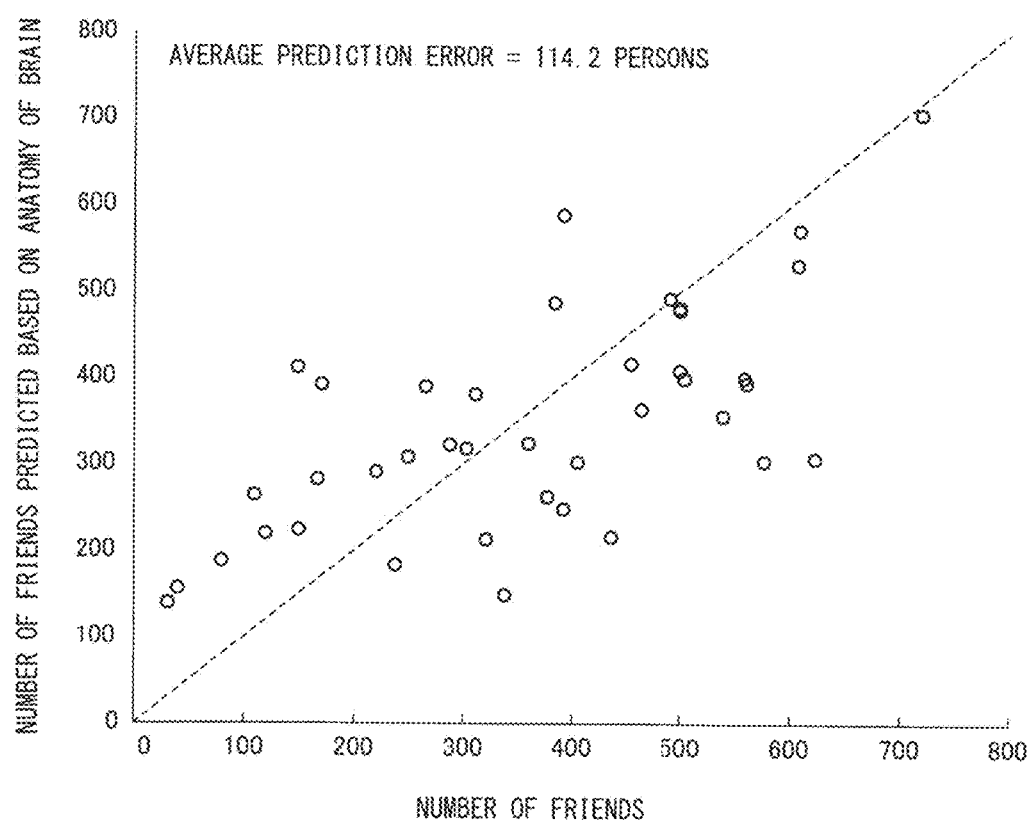

INDIVIDUAL-CHARACTERISTIC PREDICTION SYSTEM, INDIVIDUAL-CHARACTERISTIC PREDICTION METHOD, AND RECORDING MEDIUM

TECHNICAL FIELD

The present invention relates to an individual-characteristic prediction system and an individual-characteristic prediction method using images obtained by photographing a brain, and a recording medium having a program recorded thereon.

BACKGROUND ART

In recent years, a brain dock (brain medical checkup) using MRI (Magnetic Resonance Imaging) or CT (Computed Tomography) has been widely performed. In the brain dock, cross-section images of a brain are obtained by MRI or CT, and the state of the brain is determined based on the cross-section images of the brain. By performing the brain dock, it is possible to know the state of the blood vessels in the brain and thereby find signs of brain diseases such as brain infarction, brain hemorrhage and the like.

Further, with the cross-section images of the brain obtained by MRI or the like, it is possible to know not only the state of the blood vessels in the brain but also the state of each part of the brain, so that it is possible to also find signs of a specific disease unrelated to the blood vessels. For example, it is known that a patient with shrunken frontal lobe or the like has an increased chance of developing dementia.

Japanese Unexamined Patent Application Publication No. 2005-230456 discloses a method in which a gray matter image is created based on MRI images obtained by photographing the brain of a subject, and the created gray matter image is compared with a gray matter image of a normal person to determine the shrinkage of a specific part to thereby find signs of dementia or the like.

SUMMARY OF INVENTION

As described above, the diseases and signs possible to be diagnosed from the brain images with the prior arts mainly include the diseases associated with blood vessels (such as brain infarction), and signs of dementia (such as shrinkage in a specific part of the brain); and it is difficult to perform sophisticated analysis and diagnose of the brain based on the cross-section images of the brain.

An object of the present invention is to provide a prediction system, a prediction method and a program capable of predicting detailed individual-characteristics based on images obtained by photographing a brain.

Solution to Problem

An individual-characteristic prediction system according to the present invention includes: a brain image acquiring section adapted to acquire brain images obtained by scanning a brain of a subject whose individual-characteristics are to be detected; a three-dimensional information converting section adapted to obtain three-dimensional information of a cerebrum based on the brain images acquired by the brain image acquiring section; a characteristic value detecting section adapted to detect a plurality of kinds of characteristic values of each part of the cerebrum based on the three-dimensional information of the cerebrum obtained by the three-dimensional information converting section; a storage section adapted to store information about correlation between the characteristic values of each part of the cerebrum and abilities or qualities; an individual-characteristic predicting section adapted to compare the plurality of kinds of characteristic values detected by the characteristic value detecting section with characteristic values stored in the storage section, search out stored information having characteristic values similar to the plurality of kinds of characteristic values detected by the characteristic value detecting section, and predict the abilities or qualities of the subject based on information about the abilities or qualities of a brain having the searched out characteristic values; and an output section adapted to output information that exhibits the abilities or qualities of the subject predicted by the individual-characteristic predicting section, wherein the information about the correlation between the characteristic values of each part of the cerebrum and abilities or qualities stored in the storage section is information about a prediction model obtained by combining characteristic values of a plurality of parts, wherein the individual-characteristic predicting section is a section that compares the characteristic values of a plurality of parts of the cerebrum detected by the characteristic value detecting section with the prediction model stored in the storage section to predict the abilities or qualities of the subject, wherein one of the plurality of kinds of characteristic values detected by the characteristic value detecting section is characteristic values of each part of cerebral cortex obtained by converting the three-dimensional information of the cerebral cortex obtained by the three-dimensional information converting section based on the brain image into a spatial coordinate system of a standard brain, and detecting three-dimensional information of the cerebral cortex of the converted spatial coordinate system of the standard brain, and wherein another one of the plurality of kinds of characteristic values detected by the characteristic value detecting section is characteristic values obtained by quantifying the anatomy under the cerebral cortex based on the three-dimensional information of the cerebrum.

An individual-characteristic prediction method according to the present invention includes: brain image acquisition processing in which a brain image acquiring section acquires a brain image obtained by scanning the brain of a subject whose individual-characteristics are to be detected; three-dimensional information conversion processing in which a three-dimensional information converting section obtains three-dimensional information of a cerebrum based on the brain image acquired in the brain image acquisition processing; characteristic value detection processing in which a characteristic value detecting section detects a plurality of kinds of characteristic values of each part of the cerebrum based on the three-dimensional information of the cerebrum obtained in the three-dimensional information conversion processing; storage processing in which a storage section stores a standard value of characteristics of each part of the cerebrum and information about correlation between the characteristic values of each part of the cerebrum and abilities or qualities; individual-characteristic prediction processing in which an individual-characteristic predicting section compares the plurality of kinds of characteristic values detected in the characteristic value detection processing with characteristic values stored in the storage processing, searches out stored information having characteristic values similar to the plurality of kinds of characteristic values detected in the characteristic value detection processing, and predicts the abilities or qualities of the subject based on information about the abilities or qualities of a brain having the searched out characteristic values; and output processing in which an output section outputs information that exhibits the abilities or qualities of the subject predicted in the individual-characteristic prediction processing, wherein the information about the correlation between the characteristic values of each part of the cerebrum and abilities or qualities stored by the storage section in the storage processing is information about a prediction model obtained by combining characteristic values of a plurality of parts, wherein, in the individual-characteristic prediction processing, the individual-characteristic predicting section is an individual-characteristic prediction method to compare the characteristic values of a plurality of parts of the cerebrum detected by the characteristic value detecting section with the prediction model stored in the storage section to predict the abilities or qualities of the subject, wherein one of the plurality of kinds of characteristic values detected in the characteristic value detection processing is characteristic values of each part of cerebral cortex obtained by converting the three-dimensional information of the cerebral cortex obtained in the three-dimensional information conversion processing based on the brain image into a spatial coordinate system of a standard brain, and detecting three-dimensional information of the cerebral cortex of the converted spatial coordinate system of the standard brain, and wherein another one of the plurality of kinds of characteristic values detected in the characteristic value detection processing is characteristic values obtained by quantifying the anatomy under the cerebral cortex based on the three-dimensional information of the cerebrum.

A recording medium according to the present invention has a program recorded thereon, the program causing a computer to execute the steps of: a brain image acquisition step for acquiring a brain image obtained by scanning the brain of a subject whose individual-characteristics are to be detected; a three-dimensional information conversion step for obtaining three-dimensional information of a cerebrum based on the brain image acquired in the brain image acquisition step; a characteristic value detection step for detecting a plurality of kinds of characteristic values of each part of the cerebrum based on the three-dimensional information of the cerebrum obtained in the three-dimensional information conversion step; a storage step for storing the average value of the characteristics of each part of the cerebrum and information about correlation between the characteristic values of each part and abilities or qualities; an individual-characteristic prediction step for comparing the plurality of kinds of characteristic values detected in the characteristic value detection step with characteristic values stored in the storage step, searching out stored information having characteristic values similar to the plurality of kinds of characteristic values detected in the characteristic value detection step, and predicting the abilities or qualities of the subject based on information about the abilities or qualities of a brain having the searched out characteristic values; and an output step for outputting information that exhibits the abilities or qualities of the subject predicted in the individual-characteristic prediction step, wherein the information about the correlation between the characteristic values of each part of the cerebrum and abilities or qualities stored in the storage step is information about a prediction model obtained by combining characteristic values of a plurality of parts, wherein, in the individual-characteristic prediction step, the characteristic values of a plurality of parts of the cerebrum detected in the characteristic value detection step is compared with the prediction model stored in the storage step to predict the abilities or qualities of the subject, wherein one of the plurality of kinds of characteristic values detected in the characteristic value detection step is characteristic values of each part of cerebral cortex obtained by converting the three-dimensional information of the cerebral cortex obtained in the three-dimensional information conversion step based on the brain image into a spatial coordinate system of a standard brain, and detecting three-dimensional information of the cerebral cortex of the converted spatial coordinate system of the standard brain, and wherein another one of the plurality of kinds of characteristic values detected in the characteristic value detection step is characteristic values obtained by quantifying the anatomy under the cerebral cortex based on the three-dimensional information of the cerebrum.

With the present invention, it is possible to predict abilities or qualities of a subject based on the characteristic values of each part of the cerebrum of the subject obtained from the brain images and previously prepared information about correlation between the characteristic values of each part and the abilities or qualities. For example, if the characteristic values of a particular part of the cerebrum of the subject are larger than the average value, and if it is shown from the stored information that a brain having such characteristic values exhibits a high ability of memory and the like and a high quality of sociality and the like, than it can be predicted that the subject is likely to have such ability and quality.

BRIEF DESCRIPTION OF DRAWINGS

FIG. 4 is another flowchart showing the example of processing steps (part 2) according to the aforesaid embodiment;

FIG. 5 is a view showing a display example (part 1) of the analysis result of a brain image according to the aforesaid embodiment;

FIG. 6 is a view showing the display example (part 2) of the analysis result of the brain image according to the aforesaid embodiment;

FIG. 7 is a view showing the display example (part 3) of the analysis result of the brain image according to the aforesaid embodiment;

FIG. 11 is a graph showing an example of performing prediction using three areas according to the aforesaid embodiment.

DESCRIPTION OF EMBODIMENTS

[1. Configuration Examples of System]

An embodiment of the present invention (referred to as "present embodiment" hereinafter) will be described below with reference to the attached drawings.

Figure 1:
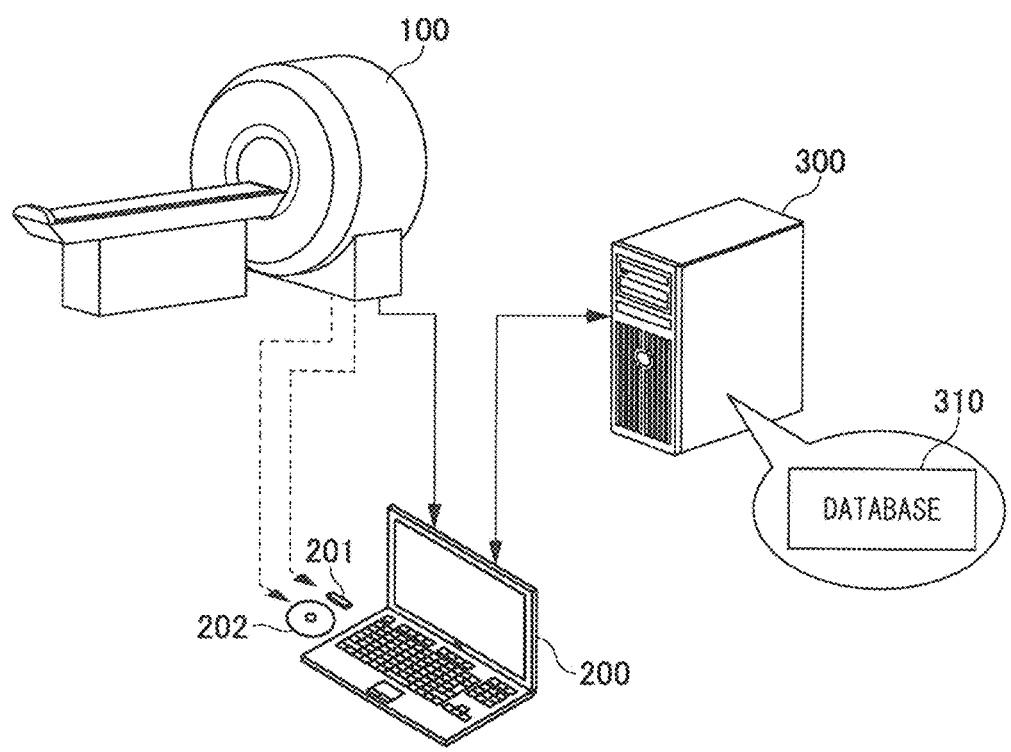
FIG. 1 is a view showing the configuration of an example of a system according to an embodiment of the present invention.

FIG. 1 is a view showing the entire configuration of a system of the present embodiment.

In the system of the present embodiment, an MRI (magnetic resonance imaging) device 100 is provided to obtain scan images of the brain of a subject whose individual-characteristics are to be detected, and the scan images of the brain (which are two-dimensional slice images) obtained by the MRI device 100 are supplied to a terminal device 200. The scan images of the brain are T1-weighted images, for example. The terminal device 200 displays and analyzes the brain images obtained from the MRI device 100. The terminal device 200 may be directly connected to the MRI device 100; however, it is also possible to transmit the scan images of the brain photographed by the MRI device 100 to the terminal device 200 via some kind of network, for example, if the terminal device 200 is located at a remote place. Alternatively, as shown in FIG. 1, it is also possible to mount a storage medium, such as a memory card 201 or an optical disk 202, on the terminal device 200, and the terminal device 200 acquires the scan images of the brain stored in the memory card 201 or the optical disk 202.

When analyzing the brain images acquired from the MRI device 100, the terminal device 200 performs communication with a server 300 to acquire data necessary for performing analysis. The server 300 is provided with a database 310 that holds a large amount of data about brain images, and the terminal device 200 acquires necessary data from the database 310 of the server 300. The individual-characteristics of the subject for whom the brain images have been photographed are detected based on the result of the analysis performed by the terminal device 200, and the detection result is displayed by the terminal device 200. The brain images accumulated by the database 310 of the server 300 are each added with data about the individual-characteristics of the subject for whom the brain images are photographed. Concrete examples of the individual-characteristics of the subject will be described later. The individual-characteristics of the subject includes data about nature and personality of the subject, and it is preferred that such data is as detailed as possible.

Note that the configuration shown in FIG. 1 is merely an example, and the present invention also includes a configuration in which the terminal device 200 is provided with a not shown database (a storage device), instead of the database 310 of the server 300. Further, it is also possible to send the brain images from the terminal device 200 to the server 300, so that the server 300 performs analysis, and the terminal device 200 displays the analysis result.

[2. Configuration Examples of Terminal Device]

Figure 2:
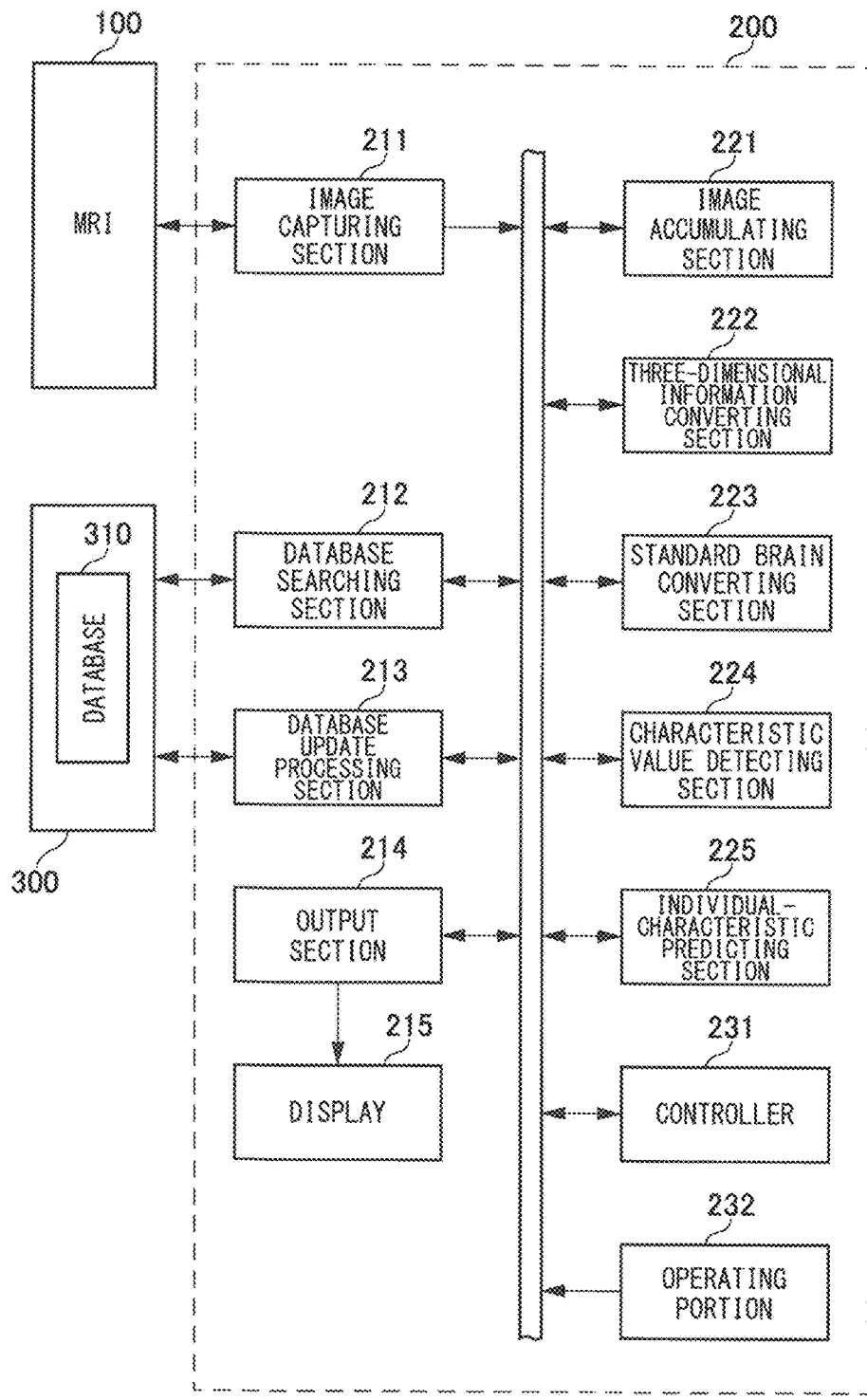
FIG. 2 is a block diagram showing a configuration example of the system according to the aforesaid embodiment.

FIG. 2 shows a configuration example of the terminal device 200. The terminal device 200 is composed of a computer device, for example. The terminal device 200 stores data stored in a memory or a hard disk drive, and performs arithmetic processing following a program. Further, the terminal device 200 performs processing to output the result of the arithmetic processing to a display device.

FIG. 2 is a function block diagram viewed from the perspective of data processing function in the terminal device 200. Data can be mutually transferred between respective processing sections.

The brain image data transmitted from the MRI device 100 or the brain image data obtained from the storage medium is taken into the terminal device 200 by an image capturing section 211 which is equivalent to a brain image acquiring section for performing brain image acquisition processing. The image capturing section 211 sends the brain image data acquired from the MRI device 100 to an image accumulating section 221. The image accumulating section 221 performs storage processing to store the obtained brain image data. Incidentally, the brain image data transmitted from the MRI device 100 is, for example, images obtained by scanning cross-sections of the brain, and is images formed by a large amount of brain image data obtained at different cross-sections for each subject.

The brain image data stored by the image accumulating section 221 is converted into three-dimensional information of the brain by a three-dimensional information converting section 222 adapted to perform three-dimensional information conversion processing. For example, the three-dimensional information converting section 222 converts the brain image data obtained at a large number of different cross-sections into three-dimensional surface layer information of surface layer (i.e., the cerebral cortex spreading on the surface of the cerebrum). The three-dimensional surface layer information converted by the three-dimensional information converting section 222 includes information about thickness of the surface layer (i.e., the cerebral cortex) of each position, and information about the curvature, the surface area, and the volume and the like of each part. Further, the three-dimensional information converting section 222 acquires information about local volume and the like of each part of the brain from the three-dimensional information of the brain.

A standard brain converting section 223 converts the three-dimensional surface layer information obtained by the three-dimensional information converting section 222 into three-dimensional surface layer information established in a spatial coordinate system aligned to the template of a standard brain. Further, the standard brain converting section 223 converts the information about the local volume and the like of each part of the brain into information about the local volume and the like aligned to the template of the standard brain. The three-dimensional surface layer information and the information about the local volume and the like established in the spatial coordinate system of the standard brain converted by the standard brain converting section 223 are stored in the image accumulating section 221. Other information, such as thickness of the cerebral cortex, the curvature, the surface area and the like of each part, is also stored in the image accumulating section 221. The three-dimensional surface layer information and the information about the local volume and the like of the standard brain stored in the image accumulating section 221 are used to perform analysis processing of the individual-characteristics.

A characteristic value detecting section 224 for performing characteristic value detection processing reads out information stored in the image accumulating section 221, and detects various characteristics indicated by the read out information, wherein the information stored in the image accumulating section 221 includes the three-dimensional surface layer information established in the spatial coordinate system of the standard brain and the like. To be specific, the thickness of each part of the cerebral cortex, and the curvature, the surface area, the volume and the like of each part are detected by the characteristic value detecting section 224. For example, the volumes of the hippocampus, the amygdala, the basal ganglia and the like are detected.

Further, the characteristic value detecting section 224 acquires the average value of each of the detected characteristics, and calculates the difference between the detected value and the average value. Incidentally, the average value of each characteristic is, for example, acquired by the characteristic value detecting section 224 from the database 310 of the server 300, and stored in a storage section (not shown). Using the average value is merely an example; other value may also be used, as long as such value serves as a standard (i.e., a standard value) when performing comparison. At this time, the average value (the standard value) to be used may vary from condition to condition of the subject, such as age, sex, location and the like.

Further, the terminal device 200 includes a database searching section 212 adapted to search the brain image data accumulated by the database 310 of the server 300, and the data added to the brain image data. The database 310 of the server 300 contains various prediction models built based on the data of the brain images obtained in the past. The brain image data of each prediction model is added with individual-characteristic data, such as individual abilities, qualities and the like, of the pertinent person previously judged based on a psychological test and/or the like. Note that, when using the term "individual abilities and qualities" in the description below, it includes various individual abilities and qualities such as IQ, attentiveness, memory, sociality, disease, personality, sense of value, and the like.

Further, the database searching section 212 compares each characteristic acquired by the characteristic value detecting section 224 with the prediction models to search out and acquire similar prediction model(s). At this time, for example, the database searching section 212 may acquire one or more similar prediction model(s) for each part of the brain.

The prediction model (s) built based on the brain image data searched out by the database searching section 212 and data of characteristic values of the subject detected by the characteristic value detecting section 224 are supplied to an individual-characteristic predicting section 225. The individual-characteristic predicting section 225 compares the brain image data of the subject whose characteristic values are acquired by the characteristic value detecting section 224 with the prediction model(s) supplied from the database searching section 212, to thereby perform individual-characteristic prediction processing to predict the individual-characteristics. The individual-characteristic predicting section 225 judges the degree of similarity between the patterns of the both, and determines, based on the degree of similarity, referable individual-characteristics indicated by the individual-characteristic data added to the brain image data supplied from the database searching section 212. Further, the individual-characteristic predicting section 225 combines a plurality of referable individual-characteristics to predict the individual-characteristics of the subject. Concrete examples of predicting the individual-characteristics will be described later.

The individual-characteristic predicting section 225 supplies the individual-characteristic data to an output section 214. The output section 214 creates display data for displaying a list of the predicted individual-characteristics, and displays the created display data on a display 215. Alternatively, the output section 214 may also output the created individual-characteristic data to the outside of the terminal device 200 under the control of a controller 231. When outputting the created individual-characteristic data to the outside, the data may be sent as attached data of an e-mail to an assigned address, for example. The display of the list of the predicted individual-characteristics is equivalent to a notification of the prediction result of the individual-characteristics of the subject.

Based on the difference of the characteristic values calculated by the characteristic value detecting section 224, the output section 214 creates a brain image of the subject in a manner in which the part(s) where the thickness or size of the cerebral cortex is(are) relatively largely deviated from the standard can be recognized. For example, the output section 214 creates a brain image in which part (s) having thick cerebral cortex is (are) colored differently from other parts. Further, the brain image created in the manner in which the part(s) where the thickness or size of the cerebral cortex is relatively largely deviated from the standard can be recognized is displayed in the display 215. Alternatively, at this time, the display may also be performed in a manner in which the degree of brain shrinkage, the amount of asymptomatic white matter lesion and/or the like is quantified, and examples of such display will be described later.

Incidentally, the processing of each of the processing sections 211-215 and 221-225 of the terminal device 200 described above is performed under the control of the controller 231. Further, the terminal device 200 is provided with an operating portion 232 (such as a keyboard, a mouse and/or the like) to be operated by an operator; and the processing of acquiring brain images, the processing of detecting characteristic values, the processing of detecting individual-characteristic and the like are performed based on the operation performed with the operating portion 232.

Further, the terminal device 200 is provided with a database update processing section 213. The database update processing section 213 updates the data stored in the database 310 based on the analysis results of the brain image obtained from other processing sections, such as the characteristic value detecting section 224, the individual-characteristic predicting section 225 and the like, of the terminal device 200.

[3. Processing Examples of Terminal Device]

Figure 3:
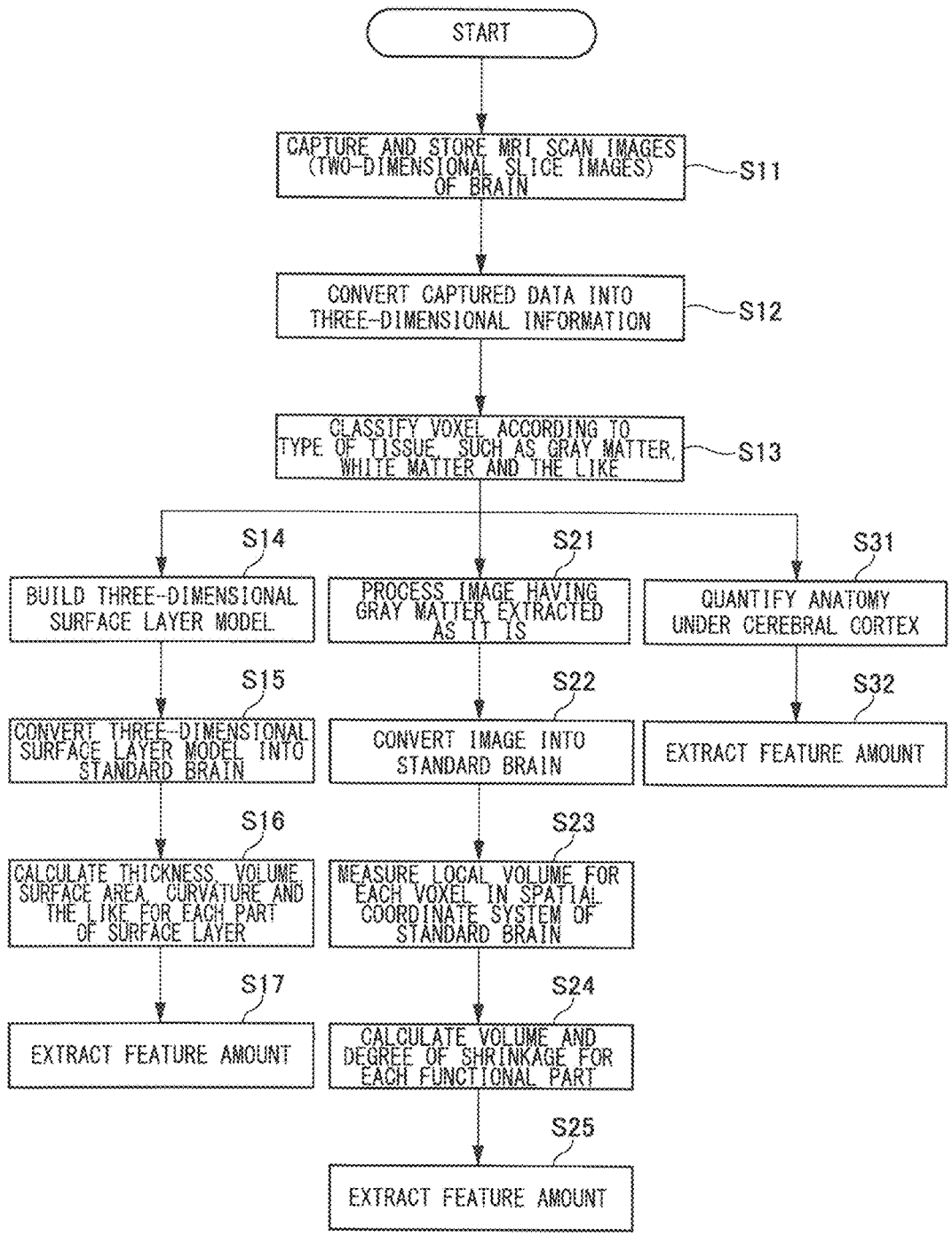
FIG. 3 is a flowchart showing an example of processing steps (part 1) according to the aforesaid embodiment.

FIG. 3 is a flowchart showing the flow of the detection processing of the brain of the subject performed in the terminal device 200.

First, the image capturing section 211 of the terminal device 200 captures the scan images of the brain (which are two-dimensional slice images) from the MRI device 100, and the image accumulating section 221 stores the captured image data (Step S11). The configuration in which the terminal device 200 directly captures the images from the MRI device 100 is merely an example; and the terminal device 200 may also, for example, capture the scan images of the brain created by the MRI device 100 or the like from a storage medium, such as a memory card, an optical disk or the like. Next, the three-dimensional information converting section 222 converts the set of the captured scan images of the brain into three-dimensional information (Step S12). Further, the three-dimensional information converting section 222 classifies each voxel of the three-dimensional brain image according to the type of tissue, such as gray matter, white matter, and the like (Step S13). After classifying each voxel of the three-dimensional brain image according to the type of tissue, three kinds of processing are performed in the terminal device 200, wherein the three kinds of processing are: processing of surface layer information of the cerebral cortex, processing with three-dimensional brain image, and processing of the anatomy under the cerebral cortex.

First, the processing of surface layer information of the cerebral cortex will be described below.

The three-dimensional information converting section 222 builds a three-dimensional surface layer model of the cerebral cortex based on the three-dimensional brain image (Step S14). The standard brain converting section 223 converts the three-dimensional surface layer information converted by the three-dimensional information converting section 222 into three-dimensional surface layer information established in the spatial coordinate system of the standard brain (Step S15). Based on the three-dimensional surface layer information of the standard brain, the characteristic value detecting section 224 detects the characteristic values of each part of the brain of the subject, and calculates the differences of the detected characteristic values from the averages (the standards) (Step S16). Examples of the characteristic values of each part include, for example, the thickness, the volume, the surface area, the curvature and the like of each part of the surface layer. The characteristic value detecting section 224 extracts the characteristic values obtained above as an individual feature amount (Step S17).

Next, the processing with three-dimensional brain image will be described below.

The three-dimensional information converting section 222 creates a three-dimensional brain image having gray matter extracted (Step S21). The standard brain converting section 223 acquires the three-dimensional brain image having gray matter extracted, and converts the acquired three-dimensional brain image into three-dimensional surface layer information established in the spatial coordinate system of the standard brain (Step S22). Further, the standard brain converting section 223 calculates the volume and the degree of shrinkage of each voxel in the spatial coordinate system of the standard brain (Step S23), and extracts a feature amount resulting from the calculated volume and degree of shrinkage of each part (Step S24).

Next, the processing of the anatomy under the cerebral cortex will be described below.

The three-dimensional information converting section 222 quantifies the anatomy under the cerebral cortex based on the three-dimensional brain image (Step S31). Further, the three-dimensional information converting section 222 extracts, from the quantified anatomy under the cerebral cortex, the volume of each part as a feature amount (Step S32).

After completing the processing for extracting the aforesaid feature amounts, the individual-characteristic predicting section 225 performs the individual-characteristic prediction processing, and the display 215 displays the prediction result. FIG. 4 is a flowchart showing the flow of the prediction processing and the display processing.

First, the individual-characteristic predicting section 225 acquires the feature amounts obtained in Steps S17, S25 and S32 of the flowchart shown in FIG. 3 (Step S41). Further, the individual-characteristic predicting section 225 compares the acquired feature amounts with feature amounts of the brain image of the prediction model(s) searched out by the database searching section 212 (Step S42). Based on the comparison, the individual-characteristic predicting section 225 predicts the individual-characteristics of the subject (Step S43). For example, if the feature amounts of a certain part of the brain of the subject are similar to the feature amounts of a specific prediction model, an individual-characteristic largely involved with the aforesaid part will be predicted as the individual-characteristic of the subject. At this time, the individual-characteristics may be directly predicted based on the feature amounts of each part of the brain; however, it is preferred that balance, combination and the like of a plurality of predetermined parts are comprehensively determined to thereby predict the individual-characteristics. The display 215 displays the list of predicted individual-characteristics (Step S44).

Further, the individual-characteristic predicting section 225 compares the size of each part obtained in Steps S17, S25 and S32 of the flowchart shown in FIG. 3 with the data of other persons in the database 310 (Step S51). Based on the comparison result obtained by the individual-characteristic predicting section 225, the output section 214 creates a brain image in a manner in which the part(s) whose size is larger and/or smaller than the average can be recognized (Step S52). The display 215 displays the created brain image (Step S53). At this time, for example, the part (s) whose size is larger than the average is(are) indicated in red color, and the part(s) whose size is smaller than the average is(are) indicated in blue color.

Incidentally, the display of the individual-characteristic in Step S44 and the display of the brain image in Step S53 may also be performed at the same time. Alternatively, either the individual-characteristics or the brain image may be selectively-displayed according to the operation performed by the user. Display examples of the individual-characteristic and the brain image will be described later. Incidentally, in addition to being displayed on the display 215, the prediction result of the individual-characteristics of the subject may also be printed out by a printer (not shown), or be outputted to the outside of the terminal device 200.

After displaying the individual-characteristic in Step S44 and displaying the brain image in Step S53, the controller 231 of the terminal device 200 judges whether or not there is data of a psychological test performed on the subject (Step S61). The psychological test described here is a test prepared in advance for assessing the individual-characteristics, such as personality and the like. Regarding the test for accurately assessing the individual-characteristics, such as personality and the like, there are various kinds of publicly known tests.

If there is data of the psychological test, the database update processing section 213 will perform update processing to add the result of the psychological test to the data of the brain image having the feature amounts obtained in the processing having been performed so far, and add the resultant data to the database 310 (Step S62).

While if there is no data of the psychological test, the update processing of the database 310 in Step S62 will not be performed.

[4. Display Examples of Analysis Result]

FIGS. 5 to 8 are views showing display examples of the analysis result of the brain image. In the present embodiment, the analysis result is indicated by three screens, which are a "profile" screen, a "brain ranking" screen, and a "see your brain" screen. The three screens can be selected by operating the operating portion 232, for example.

FIG. 5 shows a display example of the "profile" screen.

In the display example of the "profile" screen shown in FIG. 5, "prediction result of basic information", "results of brain health test", "empathy predicted based on brain", "cognition predicted based on brain" and "overall personality predicted based on brain" are displayed as items of "profile predicted based on brain image".

The item "prediction result of basic information" includes brain age and brain sex. The brain sex is assessed as degree of masculinity or femininity indicated in percentage.

The item "results of brain health test" includes degree of brain shrinkage, and whether there is white matter lesion. The degree of brain shrinkage is indicated in percentage, and also indicated is a value that shows the shrinkage is equivalent to the average of what age.

The item "empathy predicted based on brain" shows, in the form of a bar graph, the empathy predicted based on brain characteristics. FIG. 5 shows an example in which the empathy is assessed on the following points in percentage: "analyze and think about things from the other people's perspective"; "feel other people's pain as your own"; "tend to be absorbed in a story or the like with strong imagination"; and "tend to have compassion for other people's feelings". For example, in the predicted empathies, the empathy with high (or low) value is selected to be displayed.

The item "cognition predicted based on brain" shows, in the form of a bar graph, "performance IQ", "verbal IQ", "working memory capacity" and "attentiveness in daily life". The bar graph indicates each of these points in percentage.

The term "overall personality predicted based on brain" shows, in the form of a regular polygon (regular pentagon) radar chart, "curiosity", "seriousness", "sociability", "cooperativeness" and "emotional instability". The radar chart indicates each of these points in percentage.

FIG. 6 shows a display example of the "brain ranking" screen.

The "brain ranking" screen displays parts where the brain volume is larger than average and parts where the brain volume is smaller than average, in terms of rankings.

In the example shown in FIG. 6, the "brain ranking" screen displays "top 3 of your brain volume" and "bottom 3 of your brain volume".

In the example shown in FIG. 6, the rankings of the "top 3 of your brain volume" are: Rank 1st: the hippocampus; Rank 2nd: the superior parietal lobule; and Rank 3rd: the peripheral area of calcarine sulcus. Further, in the example shown in FIG. 6, the rankings of the "bottom 3 of your brain volume" are: Rank 1st: the precuneus; Rank 2nd: the superior temporal sulcus; and Rank 3rd: the orbitofrontal cortex.

Each item of the "top 3" and "bottom 3" shows the rank of the volume among 100 persons, and also explains what role the part plays. Further, if clicking "see more" button, parts lower than rank 3 are displayed.

Figure 8:
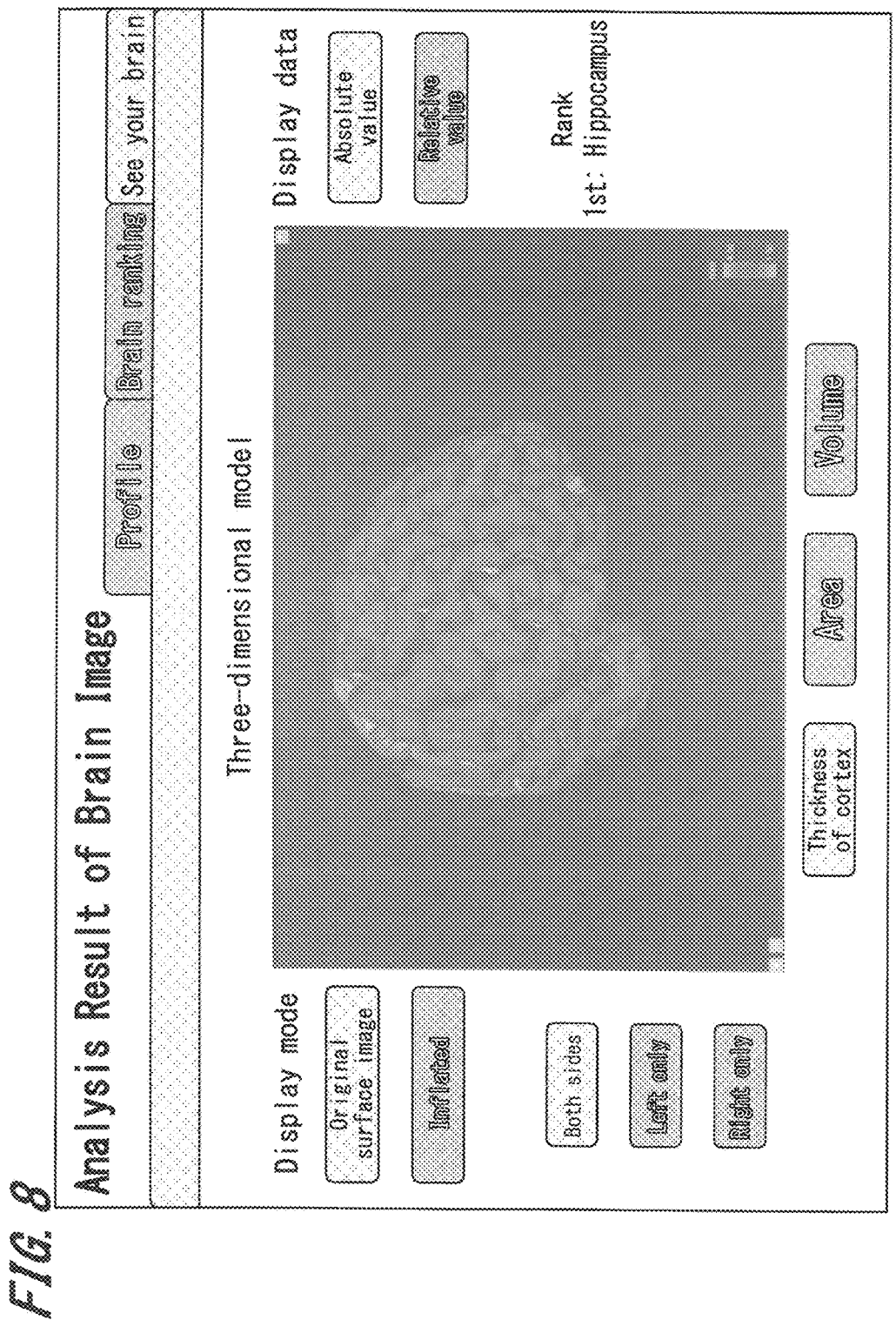
FIG. 8 is a view showing the display example (part 4) of the analysis result of the brain image according to the aforesaid embodiment.

FIGS. 7 and 8 show a display example of the "see your brain" screen. In the "see your brain" screen, brain image(s) are displayed. FIG. 7 shows an example in which a two-dimensional display is performed. When performing the two-dimensional display, the position of the cross-section of the brain can be arbitrarily changed by operating buttons of upper/lower•right/left•front/rear on the screen. Further, switching can be made between T1-weighted image, T2-weighted image, and FLAIR image. In the display example shown in FIG. 7, the parts where the volume is larger or the parts where the volume is smaller shown in the "brain ranking" screen can be indicated in different color from the other parts.

FIG. 8 shows an example in which a three-dimensional model is displayed. When displaying the three-dimensional model, display mode can be switched to a mode in which the cerebral cortex is displayed in an inflated manner. Further, when displaying the three-dimensional model, the parts where the volume is larger or the parts where the volume is smaller shown in the "brain ranking" screen may also be indicated in different color from the other parts.

[5. Examples of Prediction Based on Volume of Each Part of Brain]

Details about how to correctly predict the individual-characteristics with the individual-characteristic predicting section 225 of the terminal device 200 on the basis of the characteristic values and volume of each part detected based on the brain images will be described below.

Figure 9:
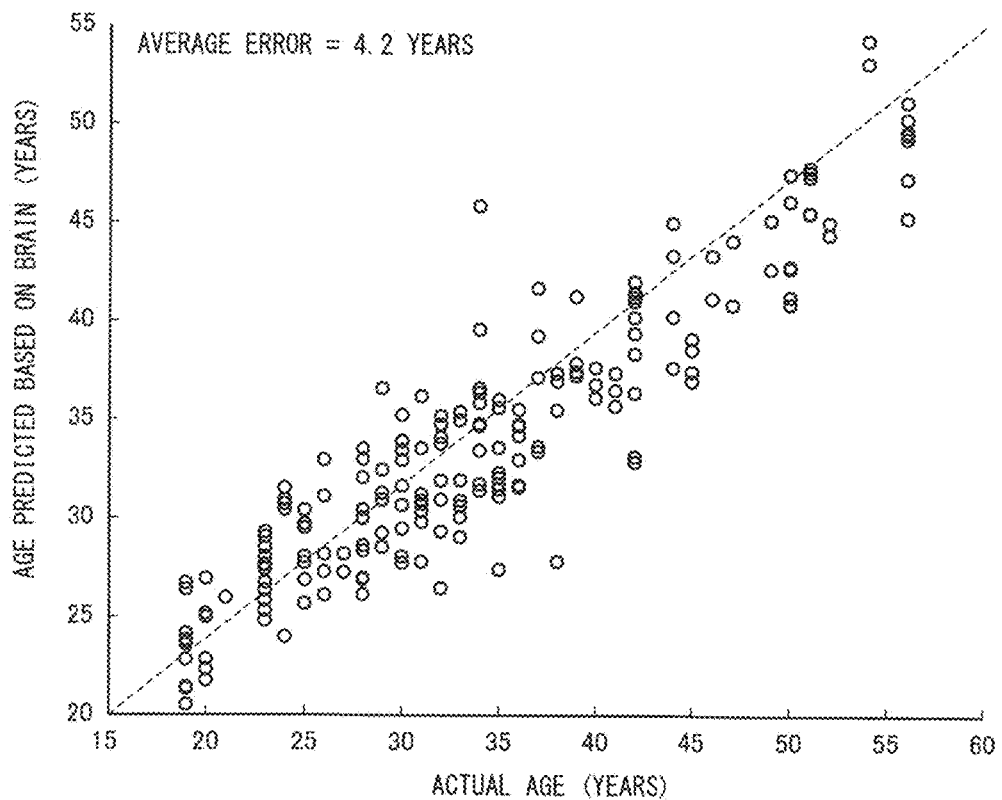
FIG. 9 is a graph showing an example of predicting the age of a subject based on volume information of each part of the brain of the subject according to the aforesaid embodiment.

FIG. 9 shows an example obtained by comprehensively building a prediction model on the basis of the volume of each part of the brain, predicting the age of the subject based on the built prediction model, and graphically showing the predicted age and the actual age of the subject. In the graph shown in FIG. 9, the vertical axis represents the age predicted from the brain, and the horizontal axis represents the actual age.

The example shown FIG. 9 is a result obtained by calculating the volume of each part of the brain based on data of brain images of about 200 subjects, and using the volume as a feature amount to predict the age. As can be known from FIG. 9, the average error between the predicted age and the actual age is 4.2 years, which means the age can be predicted with very high accuracy.

In order to easily understand prediction results, FIG. 9 shows an example in which the age is predicted; however, it is also possible to perform prediction with high accuracy in the case where an individual-characteristic (such as the cognition, the personality or the like) is predicted based on the brain image.

[6. Examples of Performing Prediction Using Three Parts with High Correlation]

When predicting an individual-characteristic (such as the cognition, the personality or the like) based on the brain image, the characteristics of a plurality of parts may be used in order to improve prediction accuracy, and concrete examples thereof will be described below with reference to FIGS. 10, 11, 12A, 12B and 12C.

Here, with regard to a subject for whom the brain image has been photographed, correlation between number of friends of the subject predicted based on his (or her) individual-characteristic and number of friends of the subject actually registered with social network service will be described below.

Figure 10:
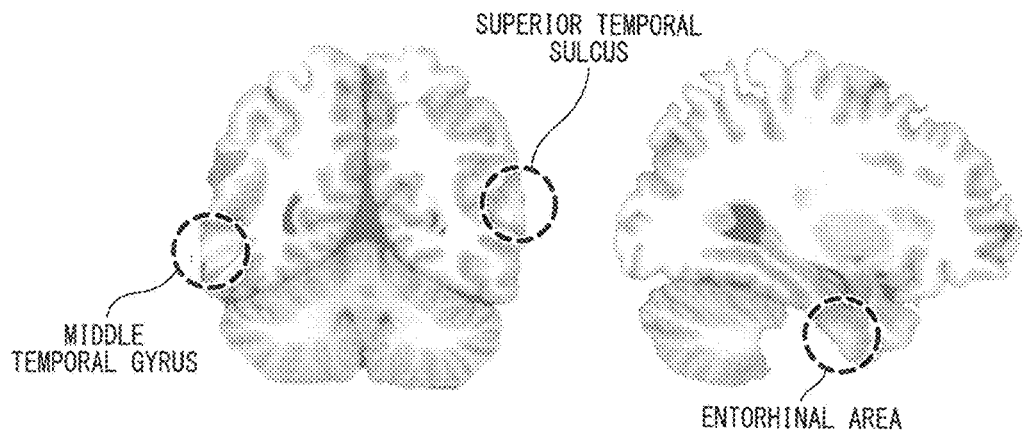
FIG. 10 is a view showing three areas of a brain.

FIG. 10 shows three parts highly correlated with the number of friends. To be specific, it is known that three parts surrounded by broken lines in the brain image shown in FIG. 10, i.e., the middle temporal gyrus, the superior temporal sulcus and the entorhinal area, are highly correlated with the number of friends.

The characteristics (such as volume and the like) of the three parts are comprehensively determined to predict the number of friends, and the correlation between the predicted number of friends (vertical axis) and the number of friends actually registered with social network service (horizontal axis) is shown in FIG. 11. It is shown that, in a range between 100 persons and 700 persons, the average predictive error between the prediction result and the actual number of friends is 114 persons, which means it is possible to perform prediction with high accuracy.

Figure 12A:
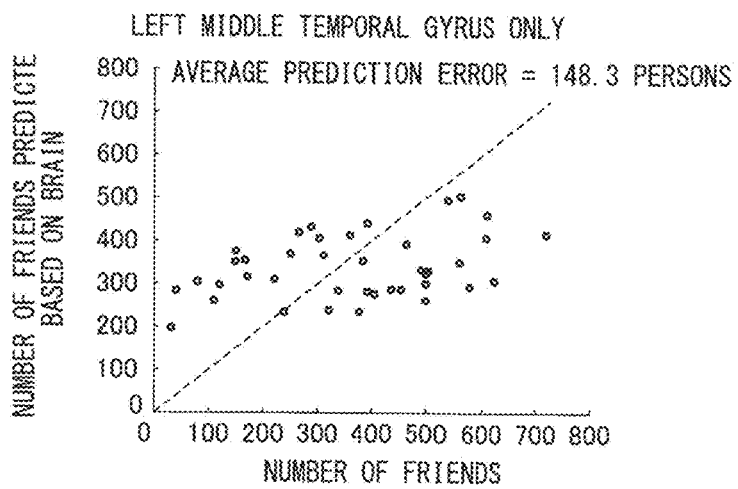
FIGS. 12A, 12B and 12C are graphs showing an example in which prediction is performed using the three areas individually according to the aforesaid embodiment.
Figure 12B:
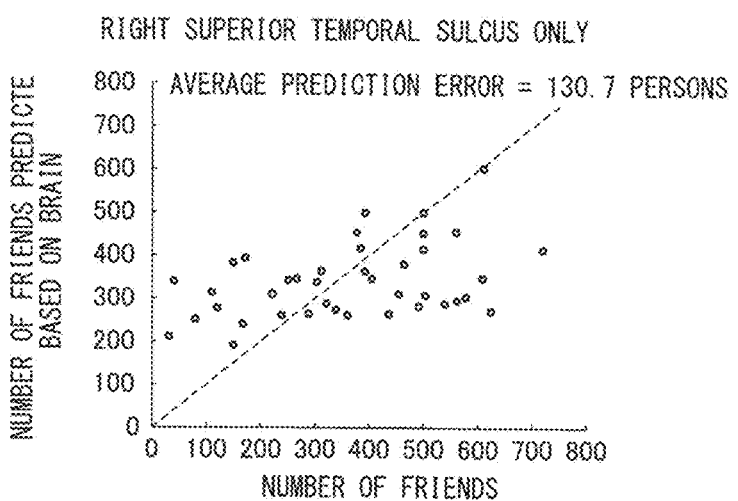
Figure 12C:
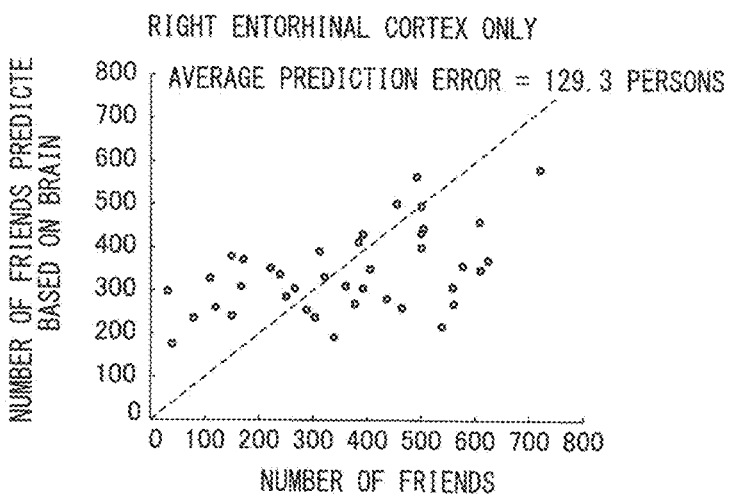

FIGS. 12A, 12B and 12C show cases where the middle temporal gyrus, the superior temporal sulcus, and the entorhinal area are individually determined, and correlations between the number of friends (vertical axis) predicted based on these parts and the actual number of friends.

As shown in left side of FIGS. 12A, 12B and 12C, in the prediction obtained by using the characteristic of the (left) middle temporal gyrus only, the average predictive error is about 148 persons.

As shown in the central part of FIGS. 12A, 12B and 12C, in the prediction obtained by using the characteristic of the (right) superior temporal sulcus only, the average predictive error is about 130 persons.

As shown in left side of FIGS. 12A, 12B and 12C, in the prediction obtained by using the characteristic of the (right) entorhinal area only, the average predictive error is about 129 persons.

As can be known by comparing FIGS. 12A, 12B and 12C with FIG. 11, in the case where the characteristics of the three parts are comprehensively determined to predict the number of friends, the difference between the predicted number of friends and the number of friends actually registered with social network service is smallest, and the prediction is very accurate.

In order to easily understand prediction results, FIGS. 10, 11, 12A, 12B and 12C show an example in which the number of friends is predicted; however, in the case where an individual-characteristic (such as empathy, cognition or the like) described in the analysis result shown in FIG. 5 is predicted, accuracy of the analysis result may also be improved by comprehensively determining the characteristics of a plurality of parts of the brain.

Incidentally, as a concrete example of performing processing for comprehensively determining the characteristics of a plurality of parts of the brain, it is possible to use a machine learning method to create a prediction model in which the characteristic values of the plurality of parts are combined, for example. Examples of the machine learning method include a method called "support vector regression".

With regard to the individual-characteristics possible to know from the characteristics of each part of the brain such as volume, thickness of cerebral cortex and the like, it has been known, as a result of research in recent years, that the thickness of each part of the cerebral cortex is correlated with IQ, attentiveness, memory, sociality, disease, personality, sense of value, quality and the like of the subject.

Here, examples of the sociality include empathy, feeling of loneliness, number of friends, being optimistic or pessimistic, criminogenic risk, prone to traffic accidents, and the like.

The disease means whether or not there is a possibility of a disease directly or indirectly associated with the brain of the subject, such as Alzheimer's disease, depression, schizophrenia and the like.

The personality means whether the subject tends to be cheerful, gloomy, worrying or the like.

The sense of value means whether the subject is devoted to his (or her) family, is fair, is politically right-leaning or left-leaning, and the like.

The quality means vocational aptitude, talent in a particular area, and the like.

The individual-characteristics described above are listed as examples; it is also possible to predict other individual-characteristics.

As described above, with the system of the present embodiment, it is possible to use the brain images obtained by scanning a brain with an MRI or the like to detect various individual-characteristics of the subject, such as personality, sociality and the like. Thus, when performing a medical examination of so-called brain dock (brain medical checkup) to diagnose diseases possible to be directly determined from brain images, for example, it is possible to use the obtained brain images to perform detection processing of the individual-characteristics to thereby know the details about the personality, the qualities and/or the like of the subject, which cannot be known with a conventional method. Particularly, by using a great number of brain images prepared in the database and the characteristics of each part of the brain obtained based on the brain images to predict the individual-characteristics, it becomes possible to detect extremely detailed characteristics, which cannot be known from a conventional examination based on brain images.

Further, by displaying a brain image from which the part(s) thought to be better than the average can be known, when notifying the subject of his (or her) individual-characteristics, since the support of the notification is clearly indicated in the brain image, it becomes possible to more effectively present the individual-characteristics to the subject.

Further, since it is possible to use the system of the present embodiment to detect the individual-characteristics, the subject having been notified of his (or her) individual-characteristics can receive training based on the notified individual-characteristics, and therefore it is possible to effectively receive training. For example, as one of individual-characteristics, if the subject is notified that he (or her) has poor memory, the subject can receive training to improve his (or her) memory.

Further, by letting the subject to receive the training for a predetermined period and then receive the detection processing of the individual-characteristics again to see whether or not there is change in each part associated with the memory, it is possible to know whether or not the training is effective, so that it is possible to more effectively perform training. Conventionally, various training methods have been proposed to improve the abilities of the brain, such as memory and the like, but it is difficult to objectively determine the effect of each training method. However, with the system of the present embodiment, it becomes possible to simply know the effect of the training method.

[7. Modifications]

In the aforesaid embodiment, the database 310 is owned by the server 300, and the terminal device 200 uses the images obtained by the MRI device 100 and the data acquired from the database 310 to perform detection processing of the individual-characteristics. In contrast with the aforesaid embodiment, the terminal device 200 connected to the MRI device 100 may have a database, instead of the server 300, so that the individual-characteristics are analyzed by only performing arithmetic processing within the terminal device 200.

Alternatively, the terminal device 200 may only perform processing to receive the brain images from the MRI device 100 and processing to display the analysis results, and a server having a database performs arithmetic processing for analysis.

Further, the individual-characteristics described in the aforesaid embodiment are merely an example; the system of the present embodiment can predict various other individual-characteristics than the individual-characteristics described in the aforesaid embodiment, as long as such individual-characteristics have direct or indirect correlation with the brain.

Further, in the aforesaid embodiment, the individual-characteristics are detected based on the images obtained by scanning a brain with the MRI device 100; however, measurement results obtained by a measuring device other than the MRI device 100 may also be referred to when detecting the individual-characteristics. For example, genetic information of the subject is analyzed based on his (or her) blood, and individual-nature obtained from the genetic information is included to comprehensively predict the individual-characteristics of the subject. Further, other devices, such as a device for performing CT (Computed Tomography) and the like, may also be used as devices to obtain the brain images.

Note that the configuration of the terminal device 200 described in the aforesaid embodiment is merely an example, and the configuration of the terminal device is not limited to the configuration shown in FIG. 2. For example, it is also possible to install a program (software) for performing the analysis processing of the present embodiment to a general-purpose personal computer device, so that the personal computer device functions as a terminal device for performing brain analysis by executing the program. In such a case, the program is recorded in a recording medium, for example. The recording medium is mounted to the terminal device (the computer device), and the terminal device executes the program recorded on the recording medium.

REFERENCE SIGNS LIST

100 MRI device
200 terminal device
211 image capturing section
212 database searching section
213 database update processing section
214 output section
215 display
221 image accumulating section
222 three-dimensional information converting section
223 standard brain converting section
224 characteristic value detecting section
225 individual-characteristic predicting section
231 controller
232 operating portion
300 server
310 database

The invention claimed is:

1. An individual-characteristic prediction system comprising:
a memory that stores information about a correlation between characteristic values of each part of a plurality of parts of a cerebrum and abilities or qualities; and
a processor programmed to
acquire brain images obtained by scanning a brain of a subject whose individual-characteristics are to be detected;
obtain three-dimensional information of the cerebrum based on the acquired brain images;
detect a plurality of kinds of characteristic values of each part of the plurality of parts of the cerebrum based on the obtained three-dimensional information of the cerebrum;
compare the plurality of kinds of detected characteristic values with the characteristic values stored in the memory;
search out information stored in the memory having characteristic values similar to the plurality of kinds of detected characteristic values;
predict abilities or qualities of the subject based on the stored information about the abilities or qualities of a brain having the searched out characteristic values; and
output information that exhibits the predicted abilities or qualities of the subject, wherein
the stored information about the correlation between the characteristic values of each part of the plurality of parts of the cerebrum and the abilities or qualities stored in the memory is information about a prediction model obtained by combining characteristic values of the plurality of parts of the cerebrum,
the comparison includes comparing, by the processor, detected characteristic values of the plurality of parts of the cerebrum with the prediction model stored in the memory to predict the abilities or qualities of the subject,
one of the plurality of kinds of detected characteristic values is a kind of characteristic value obtained by converting three-dimensional information of a cerebral cortex of the cerebrum into a spatial coordinate system of a standard brain, and detecting three-dimensional information of the cerebral cortex based on the converted spatial coordinate system of the standard brain, and
another one of the plurality of kinds of detected characteristic values is a kind characteristic value obtained by quantifying an anatomy under the cerebral cortex based on the three-dimensional information of the cerebrum.

2. The individual-characteristic prediction system according to claim 1, wherein
another one of the plurality of kinds of detected characteristic values includes a kind of characteristic value relating to microinfarcts detected from the brain image, and
the processor is further programmed to compare detected characteristic values relating to microinfarcts with the characteristic values stored in the memory.

3. The individual-characteristic prediction system according to claim 1, wherein the processor is further programmed to generate and output, to a display, a brain image in which a part or a structure of the cerebrum whose characteristic values are deviated from an average value of the characteristic values by a predetermined amount is displayed, by the display, differently from other parts or structures of the cerebrum.

4. An individual-characteristic prediction method comprising:
storing in a memory, by a processor, information about a correlation between characteristic values of each part of a plurality of parts of a cerebrum and abilities or qualities:
acquiring, by the processor, a brain image obtained by scanning a brain of a subject whose individual-characteristics are to be detected;
obtaining, by the processor, three-dimensional information of the cerebrum based on the acquired brain image;
detecting by the processor, a plurality of kinds of characteristic values of each part of the plurality of parts of the cerebrum based on the obtained three-dimensional information of the cerebrum
comparing, by the processor, the plurality of kinds of detected characteristic values with the characteristic values stored in the memory;
searching out, by the processor, information stored in the memory having characteristic values similar to the plurality of kinds of detected characteristic values;
predicting, by the processor, abilities or qualities of the subject based on the information about the abilities or qualities of a brain having the searched out characteristic values; and
outputting, by the processor, information that exhibits the predicted abilities or qualities of the subject, wherein
the stored information about the correlation between the characteristic values of each part of the plurality of parts of the cerebrum and the abilities or qualities stored in the memory is information about a prediction model obtained by combining characteristic values of the plurality of parts of the cerebrum, the comparing includes comparing, by the processor, detected characteristic values of the plurality of parts of the cerebrum with the prediction model stored in the memory to predict the abilities or qualities of the subject,
one of the plurality of kinds of detected characteristic values is a kind of characteristic value obtained by converting three-dimensional information of a cerebral cortex of the cerebrum into a spatial coordinate system of a standard brain, and detecting three-dimensional information of the cerebral cortex based on the converted spatial coordinate system of the standard brain, and
another one of the plurality of kinds of detected characteristic values is a kind of characteristic value obtained by quantifying an anatomy under the cerebral cortex based on the three-dimensional information of the cerebrum.

5. A non-transitory, computer-readable recording medium having a program recorded thereon, the program, when executed by a computer, causing the computer to:
store, in a memory, information about a correlation between characteristic values of each part of a plurality of parts of a cerebrum and abilities or qualities:
acquire a brain image obtained by scanning a brain of a subject whose individual-characteristics are to be detected;
obtain three-dimensional information of the cerebrum based on the acquired in the brain image;
detect a plurality of kinds of characteristic values of each part of the plurality of parts of the cerebrum based on the obtained three-dimensional information of the cerebrum;
compare the plurality of kinds of detected characteristic values with the characteristic values stored in the memory:
search out information stored in the memory having characteristic values similar to the plurality of kinds of detected characteristic values;
predict abilities or qualities of the subject based on the stored information about the abilities or qualities of a brain having the searched out characteristic values; and
output information that exhibits the predicted abilities or qualities of the subject, wherein
the stored information about the correlation between the characteristic values of each part of the plurality of parts of the cerebrum and the abilities or qualities stored in the memory is information about a prediction model obtained by combining characteristic values of the plurality of parts of the cerebrum,
the comparison includes comparing, by the computer, detected characteristic values of the plurality of parts of the cerebrum with the prediction model stored in the memory to predict the abilities or qualities of the subject,
one of the plurality of kinds of detected characteristic values is a kind of characteristic value obtained by converting three-dimensional information of a cerebral cortex of the cerebrum into a spatial coordinate system of a standard brain, and detecting three-dimensional information of the cerebral cortex based on the converted spatial coordinate system of the standard brain, and
another one of the plurality of kinds of detected characteristic values is a kind of characteristic value obtained by quantifying an anatomy under the cerebral cortex based on the three-dimensional information of the cerebrum.

* * * * *